United States Patent [19]

Tu et al.

[11] Patent Number: 5,843,020
[45] Date of Patent: Dec. 1, 1998

[54] ABLATION DEVICE AND METHODS

[75] Inventors: Hosheng Tu, Tustin; Weng-Kwen Raymond Chia, Irvine, both of Calif.

[73] Assignee: Irvine Biomedical, Inc., Irvine, Calif.

[21] Appl. No.: 834,373

[22] Filed: Apr. 16, 1997

[51] Int. Cl.$^6$ ................................................. A61B 17/20
[52] U.S. Cl. ............................................... 604/22; 604/49
[58] Field of Search .......................... 604/22, 49; 606/41, 606/27–29, 31, 39, 42, 45, 167, 37, 47–49

[56] References Cited

U.S. PATENT DOCUMENTS

| | | | |
|---|---|---|---|
| 4,565,200 | 1/1986 | Cosman | 128/642 |
| 4,920,978 | 5/1990 | Colvin | 128/784 |
| 5,281,218 | 1/1994 | Imran | 606/41 |
| 5,458,597 | 10/1995 | Edwards et al. | 606/41 |
| 5,536,267 | 7/1996 | Edwards et al. | 606/41 |

*Primary Examiner*—Wynn Wood Coggins
*Assistant Examiner*—Mandel Mendez

[57] ABSTRACT

An RF ablation device has a delivery catheter with distal and proximal ends. A handle is attached to the proximal end of the delivery catheter. The delivery catheter has an electrode deployment means where said electrode deployment means includes a retractable tip section comprising a deployable electrode with portion of one side having a sharp edge. The tip section has a non-deployed state when it is positioned in the delivery catheter. On the other hand, the tip section has a distended deployed state when it is advanced out of the distal end of said delivery catheter. The deployed tip section has a preformed shape while the farther distal deployed electrode defines an ablation target along with portion of the forward side having a sharp edge on said electrode. The forward edge of the deployed electrode has a slightly curvature or an essentially straight shape. Alternatively, the forward edge of the deployed electrode has sections with plurality of concave or convex curvatures.

20 Claims, 5 Drawing Sheets

ABLATION DEVICE AND METHODS

FIELD OF THE INVENTION

The present invention generally relates to improved constructions for tissue ablation system. More particularly, this invention relates to device and methods for treatment and reduction of body tissues, such as tumors by simultaneously encircling the tumor with a sharp edge electrode and applying RF energy for ablation. The device penetrates normal tissue or passes through a natural body opening to reach the target tissue to be treated and delivers therapeutic energy to the target tissue while loosens the target tissue for improved treatment. This device is suitable for reducing the mass of any type of tissue, and it is most particularly useful for treating tissue containing tumor cells and the like.

BACKGROUND OF THE INVENTION

The most popular tumor management approach is through surgical means. Surgical treatment of cellular tissues usually exposes both the target and intervening tissues to substantial trauma and causes a great deal of damage to healthy tissues. During a surgical procedure, precise placement of a treatment device is difficult because of the location of a target tissue in the body or the proximity of the target tissue to obstructions or easily damaged critical body organs, such as nerves or blood vessels. New products with an emphasis on minimally invasive approaches are being progressively developed to replace the traumatic nature of traditional surgical procedures.

There has been a relatively significant amount of activity in the area of high energy as a tool for treatment of tumors. It is known that elevating the temperature of tumors is helpful in the treatment and management of cancerous tissues. The mechanisms of selective cancer cell eradication by high energy doses are not completely understood. However, Edwards et al. in U.S. Pat. No. 5,536,267 hypothesized certain cellular effects of high energy on cancerous tissues. Nevertheless, treatment methods for applying heat to tumors include the use of direct contact radio-frequency (RF) applicators, microwave radiation, inductively coupled RF fields, ultrasound, and a variety of simple thermal conduction techniques.

In an illustrative example, high frequency currents are used in electrocautery procedures for cutting human tissues, especially when a bloodless incision is desired or when the operating site is not accessible with a normal scalpel but presents an access for a thin instrument through natural body openings such as the esophagus, intestines, uterus, or urethra. Examples include the removal of prostatic adenomas, bladder tumors or intestinal polyps. In such cases, the high frequency current is fed by a surgical probe into the tissue to be cut. The resulting dissipated heat is controlled so that no boiling and vaporization of the cell fluid occurs at this point. The frequency of the current for this use must be above ca. 300 kHz in order to avoid any adverse effect such as nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of natural body process. Ablative energy may also be controlled by a close-loop temperature control mechanism.

The same is true for ablation of the tumor itself through the use of RF energy. Different methods have been utilized for the RF ablation of masses such as tumors. Instead of heating the tumors it is ablated through the application of RF energy. This process has been difficult to achieve due to a variety of factors, such as access site, probe location, electrode positioning, energy level, at. al. Among them, the most critical factor is the positioning of the RF ablation electrode to effectively ablate all of the mass by controlled delivery and monitoring of RF energy to achieve successful ablation without damage to non-tumor tissue.

There have been a number of different treatment methods and devices for minimally invasively treating tumors. One such example is an endoscope that produces RF hyperthermia in tumors, as described in U.S. Pat. No. 4,920,978. In U.S. Pat. No. 4,920,978, an endoscope for RF hyperthermia is disclosed. In U.S. Pat. No. 4,565,200, an electrode system is described in which a single entrance tract cannula is used to introduce an electrode into a selected body site. In U.S. Pat. No. 5,458,597, an RF probe with fluid infusion capability is described. Similarly, in U.S. Pat. No. 5,536,267, a multiple electrode ablation apparatus with fluid infusion means is described. For the system with a close-loop temperature control mechanism, the fluid infusion means for the sole purpose of cooling off the tissues may not be required. Recent clinical studies have indicated that the delivered RF energy is rapidly dissipated and reduced to a non-destructive level by conduction and convection forces of natural body process. In all examples, the tissue destruction energy and/or substances have been used to destroy malignant, benign and other types of cells and tissues from a variety of anatomic sites and organs. Tissues treated include isolated carcinoma masses and target tissues in organs such as prostate, glandular and stromal nodules characteristic of benign prostate hyperplasia.

There is a need for an RF ablation apparatus that is useful for treatment and reduction of undesired body tissues by minimally invasive procedures. It would be desirable for such a device to surround the circumferential base of the tumor with treatment electrodes, and to define a controlled ablation amount of RF energy by monitoring the temperature and controlling the energy delivered. Additionally, there is a need for an ablation device with a sharp edge electrode to loosen the target tissue for improved ablation treatment. This would provide for a more effective method for reducing the mass of any type of tissue containing tumor cells and the like.

SUMMARY OF THE INVENTION

The present invention provides an improved ablation catheter which can be used in ablating a desired tissue mass, such as a tumor, in a minimally invasive manner. In one embodiment, an RF ablation device has a delivery catheter with distal and proximal ends wherein a semi-flexible insert is located within the lumen of said delivery catheter. A handle is attached to the proximal end of the delivery catheter. The semi-flexible insert that is also semi-rigid is like a wire which is made of a conductive material, such as stainless steel and has a cross-sectional shape of either circular, oval, trapezoid, diamond, or rectangular. In a further embodiment, the semi-flexible insert serves as a conducting means for the distal electrode to be connected to an external RF generator for RF energy transmission. It also serves as a semi-rigid mechanical support in advancing the ablation device during insertion and RF ablating operations. The proximal end of said insert is attached to a push-pull mechanism on the handle.

The delivery catheter has an electrode deployment means. The electrode deployment means includes a retractable tip section, which constitutes the distal part of said semi-flexible insert, comprising a farther distal deployable electrode which is joined to the tip section with a spring-loaded joint. In one embodiment, said electrode is consisted of blunt sides all around except portion of one side having a sharp edge. The sharp edge has a conductive surface for RF energy delivery while the remaining surfaces and edges are non-conductive. The tip section has a non-deployed state when it is positioned in the delivery catheter. This non-deployed state is maintained during said device insertion step into a patient and during withdrawal of the device from a patient.

In another embodiment, the tip section has a distended deployed state when it is advanced out of the distal end of said delivery catheter. Deployment of the tip section is accomplished by a pushing action on the push-pull mechanism on the handle. The deployed tip section has a pre-formed shape so that the tip section would extend outwardly to one side of said delivery catheter when deployed. In the meantime, the distal deployed electrode has a pre-equipped torsion spring so that the electrode bends inwardly to the opposite side of the delivery catheter. The deployed electrode defines an ablation target along with portion of the forward side of said electrode having a sharp edge. The forward side of the deployed electrode has a slightly circular shape, either concave or convex, to encircle the target tissue. In still another embodiment, portion of said forward side of the deployed electrode has an essentially straight edge. In a further embodiment, the forward side of the deployed electrode has sections with plurality of concave or convex curvatures to encircle the target tissue mass.

A conducting wire which is soldered to the proximal end of said insert passes through the interior void of the handle and is thereafter soldered to a contact pin of the connector at the proximal end of the handle. From there, the conducting wire is connected to an external RF generator for ablation operations. The ablation device may further comprise a steering mechanism at the handle for controlling the deflection of the distal section of the delivery catheter. Usually a rotating ring or a secondary push-pull plunger on the handle is employed as integral part of the steering mechanism. One end of the steering wire is attached at a point on the tip section of said insert while the other end is attached to the steering mechanism at the handle. The steering mechanism on a steerable catheter device is well-known to those who are skilled in the art. In an additional embodiment, the ablation device further comprises a temperature sensing and close-loop temperature control mechanism for the electrode having a temperature sensor at the tissue contact site. The location of the temperature sensor is preferably in the proximity of the sharp edge of said electrode.

The delivery catheter of said ablation device of this invention having a tip section under a non-deployed state is inserted into the body through a small surgery hole or through the natural body openings such as esophagus, intestines, uterus, or urethra. After the catheter approaches the target tissue mass to be treated, the tip section is deployed by being pushed out of the delivery catheter from a push-pull mechanism at the handle. Once positioned, the sharp edge of the electrode encircles the circumferential base of the tissue mass. By simultaneously or alternately gradually pushing forward the catheter against the tissue mass and applying RF energy, the target tissue mass is reduced and treated as a result of a combination of the RF energy and the mechanical cutting force.

In a further embodiment, the deployable electrode having a sharp edge at its forward side loosens the target tissue while delivers therapeutic energy for improved treatment. Said electrode is suitable for reducing the mass of any type of tissue, particularly effective for treating tumor tissue, such as the removal of prostatic adenomas, bladder tumors, uterus tumors, urethra's tumors, intestinal polyps and the like.

The method and apparatus of the present invention have several significant advantages over known ablation devices or ablation techniques. In particular, the electrode of an ablation device of this invention results in a more effective means for reducing the mass of any type of tissue containing tumor cells and the like.

BRIEF DESCRIPTION OF THE DRAWINGS

The features and objects of the present invention will become more apparent and the invention itself will be best understood from the following Detailed Description of the Preferred Embodiments, when read with reference to the accompanying drawings.

DETAILED DESCRIPTION OF THE PREFERRED EMBODIMENTS

Figure 1:
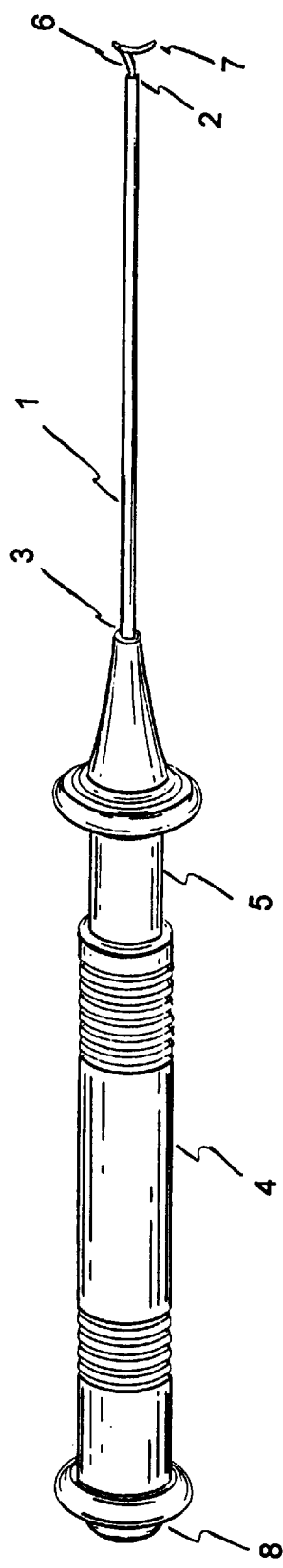
FIG. 1 is a prospective view of the ablation device having an electrode deployment means comprising a retractable tip section in accordance with the principles of the present invention.

An ablation device constructed in accordance with the principles of the present invention comprises: a delivery catheter with distal and proximal ends wherein a semi-flexible insert is located within the lumen of said delivery catheter. FIG. 1 shows a prospective view of the ablation device having a delivery catheter 1 with a distal end 2 and a proximal end 3. A handle 4 is attached to the proximal end 3 of said catheter 1. The proximal end of a semi-flexible insert is attached on a push-pull mechanism 5 at the handle 4. The distal end of said insert comprises an outwardly extended tip section 6 and a farther distal electrode 7 which is joined to said tip section by a spring-loaded joint. The semi-flexible insert serves as a conducting means for the electrode to be connected to an external RF generator. Said insert also serves as a mechanical support in advancing the ablation device during device insertion operation and during RF ablating operation.

An insulated conducting wire which is soldered to the proximal end of said semi-flexible insert passes through the interior void of the handle 4 and is thereafter soldered to a contact pin of the connector 8 at the proximal end of said handle. From there, the conducting wire is connected to an external RF generator for RF energy transmission. In a further embodiment, the ablation device may comprise a steering mechanism at the handle for controlling the deflection of the distal section of the delivery catheter 1. One end of the steering wire is attached at certain point of the tip section of said insert while the other end is attached to the steering mechanism at the handle. The steering mechanism on a steerable catheter device is well-known to those who are skilled in the art.

In an additional embodiment, the ablation device further comprises a temperature sensing and close-loop temperature control mechanism for the electrode having a temperature sensor at the tissue contact site of said electrode 7.

Figure 2:
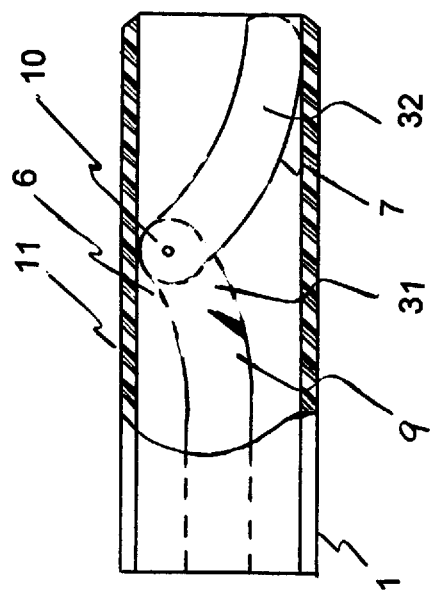
FIG. 2 is a close-up view of the retractable tip section at non-deployed state.

FIG. 2 is a close-up view of the retractable tip section at non-deployed state. The semi-flexible insert 9, having a retractable tip section 6, is located within the lumen of the delivery catheter 1. A deployable electrode 7, a two-piece electrode comprising a first piece 31 and a second piece 32 joined by a torsion spring 10, is located at the farther distal end of said tip section 6. The non-deployed state is maintained during device insertion into a patient and device withdrawal from a patient. Under non-deployed state, the tip section 6 which has a preformed shape tends to tilt to the internal surface of one side of the delivery catheter 1 while the electrode 7 which has a pre-installed torsion spring tends to tilt to the opposite side of said delivery catheter. The torsion spring is located at the joint 10 between said tip section 6 of the insert and said deployable electrode 7. Said torsion spring is positioned at the joint in a way that the spring-loaded force pushes the electrode backward when deployed. In another embodiment, the distal section 11 of said delivery catheter 1 comprises a reinforced shaft to maintain its circular cross-section shape even under the impact of the preformed tip section 6 and/or pre-equipped spring-loaded electrode 7. Reinforcement of the distal shaft of said catheter can be accomplished either by a braided tubing or a tubing with higher hardness welded to said delivery catheter 1.

Figure 3:
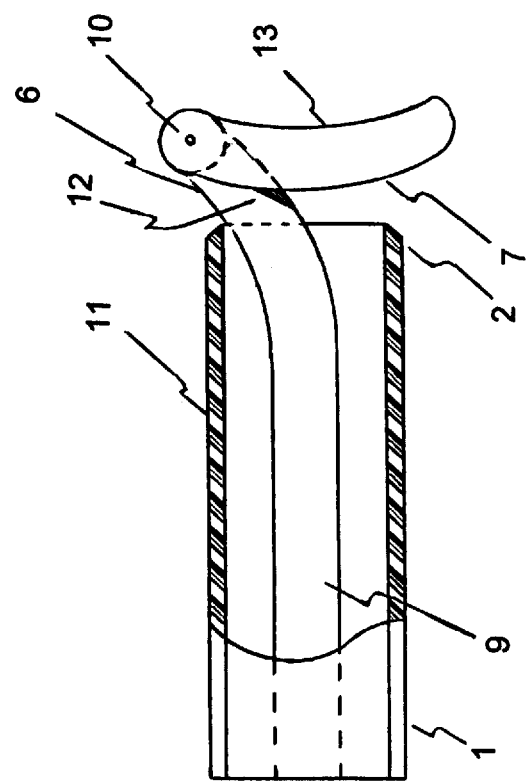
FIG. 3 is a close-up view of the retractable tip section at fully deployed state.

FIG. 3 shows a close-up view of said retractable tip section at fully deployed state. The tip section 6 has a distended deployed state when it is advanced out of the distal end 2 of said delivery catheter 1. Deployment of the tip section is accomplished by a pushing action on the push-pull mechanism at the handle. Because of its preformed shape, the first piece 31 of the two-piece electrode extends outwardly to one side of said catheter when deployed. In the meantime, second piece 32 of the two-piece electrode 7, wherein each piece has its own distal and proximal ends, and a body element having a front side extending therebetween, bends inwardly to the opposite side of said catheter because of its pre-equipped torsion spring. The spring-loaded electrode can only bend to certain position when fully deployed because of a lower stopper 12 on the tip section 6. At fully deployed state, the body element of the second piece 32 of the two-piece electrode 7 is essentially perpendicular to the delivery catheter 1, and the front side 13 of the body element facing the distal direction of the delivery catheter.

The location of the temperature sensor is preferably in the proximity of the sharp edge of said electrode. Temperature sensing wires along with a thermocouple or thermistor means are provided to transmit the temperature data from the tissue contact site to an external temperature measuring and control device. An algorithm is installed in said measuring and control device so that a close-loop temperature control is effective and the temperature data is relayed to the RF generator for controlled energy delivery.

Figure 4:
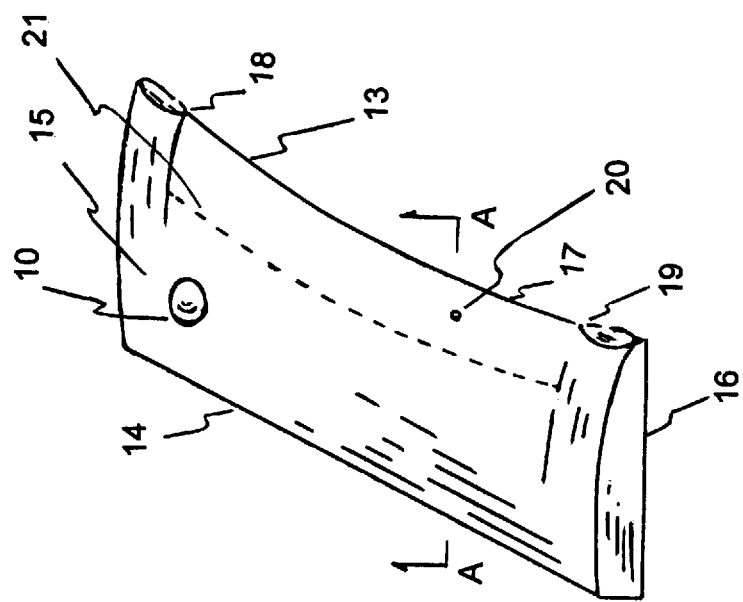
FIG. 4 is a prospective view of the deployable electrode having a sharp edge on its forward side of FIG. 3.
Figure 5:
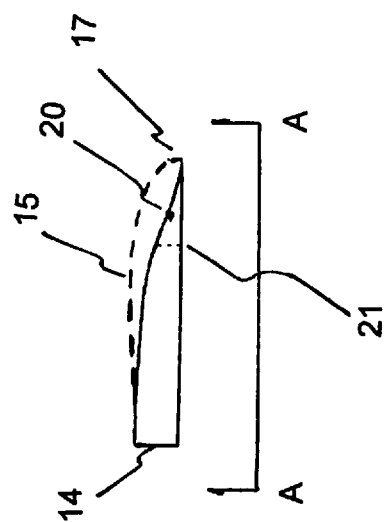
FIG. 5 is a cross-sectional view of the deployable electrode having a sharp edge on its forward side of FIG. 4.

FIG. 4 is a prospective view of the electrode having a sharp edge on its forward side while FIG. 5 shows a cross-sectional view of FIG. 4. The electrode comprises a front side 13, a backward side 14, a top side 15 and a bottom side 16. The forward side has a sharp edge 17 which is between the points 18 and 19. The front side 13 beyond the points of 18 and 19 is a blunt edge. The sharp edge may be a straight edge, a curved edge or an edge with plurality of curvatures. The surface of said electrode is coated with an insulating material except the front end of the sharp edge, where a temperature sensor 20 is located. In a particular embodiment, the front end of said sharp edge having conducting surface may range from a fractional of millimeter to several millimeters. The front end is defined as the surfaces of the top side and bottom side from the sharp edge 17 to an imaginary line 21.

As shown in FIG. 5, the sharp edge 17 is at the front side 13 of said electrode while the temperature sensor 20 is in the proximity of the sharp edge. The front end of the front side which ranges from the sharp edge 17 to the imaginary line 21, including the temperature sensor 20, has a conducting surface for RF energy delivery. From the foregoing, it should now be appreciated that an improved ablation device comprising a sharp edge electrode has been disclosed for tissue ablation procedures. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. An ablation device system comprising:
   a delivery catheter having a distal section, distal and proximal ends, and a lumen extending therebetween;
   a semi-flexible insert located inside the lumen of the delivery catheter, wherein the insert has a distal end, a proximal end, and an elongate shaft extending therebetween, and wherein the insert has a retractable tip section;
   a two-piece electrode mounted at the distal end of the insert, wherein each piece of the two-piece electrode has its own distal and proximal ends, and a body element having a front side extending thereinbetween, and wherein a first piece of the two-piece electrode is secured to the distal end of the elongate shaft while a second piece of the two-piece electrode is secured to the distal end of the first piece through a torsion spring;
   a handle attached to the proximal end of the delivery catheter, wherein the handle has a cavity;
   an electrode deployment means located at the handle, wherein the electrode deployment means is connected to the proximal end of the insert; and
   a preformed shape for the two-piece electrode of the retractable tip section, wherein the first piece extends outwardly to one side of the delivery catheter when the electrode is deployed, and wherein the second piece bends inwardly to the opposite side of the delivery catheter to expose the body element of the second piece essentially perpendicular to the delivery catheter, the front side of the body element facing the distal direction of the delivery catheter.

2. The ablation device system as in claim 1, wherein a portion of the front side of the second piece of the two-piece electrode has an essentially straight edge.

3. The ablation device system of claim 1 further comprising a steering mechanism at the handle for controlling the deflection of the distal section of the delivery catheter.

4. The ablation device system as in claim 1, wherein a portion of the front side of the second piece of the two-piece electrode has a sharp edge, and wherein the sharp edge has a conductive surface.

5. The ablation device system as in claim 1, wherein a portion of the front side of the second piece of the two-piece electrode has a slightly curved edge.

6. The ablation device system as in claim 1, wherein a portion of the front side of the second piece of the two-piece electrode has a plurality of curved edges.

7. The ablation device system of claim 4 further comprising a RF generator, wherein the RF current from the RF generator is relayed to the electrode for ablation purposes.

8. The ablation device system of claim 7 further comprising a temperature sensor mounted at the electrode and a closed-loop temperature control mechanism, wherein the temperature measured by the temperature sensor is relayed to the closed-loop temperature control mechanism and adapted for controlling the RF current delivery to the electrode.

9. A method for operating an ablation device system inside the body of a patient for treating a target tissue, the ablation device system comprising: a delivery catheter having a distal section, distal and proximal ends, and a lumen extending therebetween; a semi-flexible insert located inside the lumen of the delivery catheter, wherein the insert has a distal end, a proximal end, and an elongate shaft extending therebetween, and wherein the insert has a retractable tip section; a two-piece electrode mounted at the distal end of the insert, wherein each piece of the two-piece electrode has its own distal and proximal ends, and a body element having a front side extending therebetween, and wherein a first piece of the two-piece electrode is secured to the distal end of the elongate shaft while a second piece of the two-piece electrode is secured to the distal end of the first piece through a torsion spring; a handle attached to the proximal end of the delivery catheter, wherein the handle has a cavity; an electrode deployment means located at the handle, wherein the electrode deployment means is connected to the proximal end of the insert; a preformed shape for the two-piece electrode of the retractable tip section, wherein the first piece extends outwardly to one side of the delivery catheter when the electrode is deployed, and wherein the second piece bends inwardly to the opposite side of the delivery catheter to expose the body element of the second piece essentially perpendicular to the delivery catheter, the front side of the body element facing the distal direction of the delivery catheter; and a RF generator; the method comprising:

(a) introducing the delivery catheter having an insert under a non-deployed state into the body through a small surgery hole or through a natural body opening;

(b) once approaching the target tissue, deploying the tip section by activating the electrode deployment means at the handle;

(c) once positioning the two-piece electrode, encircling the target tissue; and (d) by a simultaneous or alternate mode, gradually pushing forward the delivery catheter from the handle against the target tissue and applying RF energy to the electrode.

10. The method for operating an ablation device system as in claim 9, wherein a portion of the front side of the second piece of the two-piece electrode has an essentially straight edge.

11. The method for operating an ablation device system as in claim 9, further comprising a steering mechanism at the handle for controlling the deflection of the distal section of the delivery catheter.

12. The method for operating an ablation device system as in claim 9, wherein a portion of the front side of the second piece of the two-piece electrode has a sharp edge, and wherein the sharp edge has a conductive surface.

13. The method for operating an ablation device system of claim 9 further comprising the forward side of the deployed electrode having a sharp edge.

14. The method for operating an ablation device system as in claim 9, wherein a portion of the front side of the second piece of the two-piece electrode has a slightly curved edge.

15. The method for operating an ablation device system as in claim 9, wherein a portion of the front side of the second piece of the two-piece electrode has a plurality of curved edges.

16. The method for operating an ablation device system of claim 9 further comprising a RF generator, wherein the RF current from the RF generator is relayed to the electrode for ablation purposes.

17. The method for operating an ablation device system of claim 10 further comprising a temperature sensor mounted at the electrode and a closed-loop temperature control mechanism, wherein the temperature measured by the temperature sensor is relayed to the closed-loop temperature control mechanism and adapted for controlling the RF current delivery to the electrode.

18. The method for operating an ablation device system of claim 16 further comprising treating target tissues by loosening the tissue and applying RF energy in a simultaneous mode, alternate mode, or a combination thereof.

19. The method for operating an ablation device system of claim 9 further comprising treating target tissues by loosening the tissue and applying microwave energy in a simultaneous mode, alternate mode, or a combination thereof.

20. The method for operating an ablation device system of claim 16 further comprising treating target tissues selected from the group of prostatic adenomas, bladder tumors, uterus tumors, urethra's tumors, or intestinal polyps by loosening the tissue and applying RF energy in a simultaneous mode, alternate mode, or a combination thereof.

* * * * *